United States Patent
Roesch et al.

(10) Patent No.: US 8,666,771 B2
(45) Date of Patent: Mar. 4, 2014

(54) HEALTHCARE SYSTEM PLANNING TOOL

(75) Inventors: Anthony Roesch, Chicago, IL (US);
Nicolas G. Bracco, Chicago, IL (US);
Todd W. Fitz, Chicago, IL (US);
Charles Siconolfi, New York, NY (US);
Lauren McKenna, Hoboken, NJ (US);
Charles H. Ingrum, St. Louis, MO (US)

(73) Assignee: HOK Group, Inc., St. Louis, MO (US)

( * ) Notice: Subject to any disclaimer, the term of this patent is extended or adjusted under 35 U.S.C. 154(b) by 40 days.

(21) Appl. No.: 13/156,031

(22) Filed: Jun. 8, 2011

(65) Prior Publication Data

US 2011/0301971 A1 Dec. 8, 2011

Related U.S. Application Data

(60) Provisional application No. 61/352,586, filed on Jun. 8, 2010.

(51) Int. Cl.
*G06Q 50/22* (2012.01)

(52) U.S. Cl.
USPC .................................................. 705/2; 703/6

(58) Field of Classification Search
USPC ............................................................ 703/6
IPC .................................. G06Q 10/00,50/00, 50/22
See application file for complete search history.

(56) References Cited

U.S. PATENT DOCUMENTS

| | | | |
|---|---|---|---|
| 5,652,717 A * | 7/1997 | Miller et al. | 703/6 |
| 6,556,878 B1 | 4/2003 | Fielding | |
| 7,856,370 B2 | 12/2010 | Katta et al. | |
| 2002/0099561 A1 | 7/2002 | Wilkins et al. | |
| 2002/0107769 A1 | 8/2002 | Dashefsky et al. | |
| 2003/0020739 A1 | 1/2003 | Cohen et al. | |
| 2005/0137929 A1 | 6/2005 | Frazier et al. | |
| 2005/0171918 A1 | 8/2005 | Eden et al. | |
| 2007/0088709 A1 | 4/2007 | Bailey et al. | |
| 2008/0205768 A1 | 8/2008 | Srivastava | |
| 2009/0138340 A1 | 5/2009 | Borr et al. | |
| 2010/0287478 A1 | 11/2010 | Avasarala et al. | |
| 2011/0077958 A1 | 3/2011 | Breitenstein et al. | |

OTHER PUBLICATIONS

Laurel Rothman, Strong Neighbourhoods Task Force Research Product Two: The Role of Community Infrastructure in Building Strong Neighbourhoods, Feb. 14, 2005, Family Service Association of Toronto, p. 3.*

* cited by examiner

*Primary Examiner* — John Pauls
*Assistant Examiner* — Jason Tiedeman
(74) *Attorney, Agent, or Firm* — Bryan W. Bockhop; Bockhop & Associates, LLC (57) ABSTRACT

A system for planning at a healthcare facility employs a database that stores health care facility impacting data including demographic data describing a preselected set of aspects of a population residing within a defined geographic area. A simulator applies modeling tools to the health care facility impacting data and generates output data corresponding to selected data in the health care facility impacting data. The modeling tools include a protocols of care tool; a service configuration modeling tool; a financial analysis tool; and a facility modeling tool. A video monitor displays an image of a map with a visual representation of the geographic area and a plurality of dynamically configurable data display objects that are superimposed on the map. Each data display object is disposed adjacent to a location of a different healthcare facility and each displays output data generated by the simulator.

20 Claims, 5 Drawing Sheets

HEALTHCARE SYSTEM PLANNING TOOL

CROSS-REFERENCE TO RELATED APPLICATION(S)

This application claims the benefit of U.S. Provisional Patent Application Ser. No. 61/352,586, filed Jun. 8, 2010, the entirety of which is hereby incorporated herein by reference.

BACKGROUND OF THE INVENTION

1. Field of the Invention

The present invention relates to healthcare systems planning tools and, more specifically, to a tool for assessment and dynamic forecasting of resources across a health system.

2. Description of the Related Art

Large institutional organizations, such as healthcare organizations, expand their capacities from time to time in response to changes in demand for their services. For example, a healthcare organization might build a new hospital in an area when it determines that the population in the area has increased to the point where it could support a new hospital. Similarly, a hospital might remodel to redeploy services to services that have experienced an increase in demand. For example, a hospital might redeploy resources from a pediatric unit to a cardiovascular unit as the average age of the surrounding population increases.

However, prior to building a new facility or expanding an existing one, the organization must consider many different factors in deciding such issues as: the level and type of demand for services; where to build the facility; the capacity of the facility, the features offered by the facility, capacity of nearby competing facilities, and the like. Such organizations also consider such factors when considering expanding or redeploying resources at existing facilities.

In the example of building a new hospital, the healthcare organization must first consider the economic impact of a new hospital and the demand for various types of services that could be offered at the hospital. This must be considered in view of such factors as: population and other demographic information, trends in demand for healthcare services in the area, services offered by competing facilities in the area, and similar factors. The organization's planners must predict the types of healthcare needs that potential patients will most likely have (e.g., if the average age in the population is low, cardiac surgery might not immediately be a high priority) and the trends in how those needs will change (e.g., as the average age increases, the facility will experience an increased demand for cardiac surgery). Planners must also predict the effects of competing facilities changing their capacity (e.g., they must determine the impact of nearby hospitals increasing their cardiac surgery capabilities). Many other factors must also be considered in the planning process in order to make an optimal decision regarding the nature of a new facility.

Typically, this type of analysis in performed by compiling data, generating estimates and making predictions based on past experience. The results of this process are presented to the planners, who then make the decisions as to how to proceed. Spreadsheets are often used to assemble the data and such spreadsheets can allow for some manipulation of data to examine several different scenarios. However, such spreadsheets display only compilations of the raw data, usually in the form of tables. Considering alternative scenarios in a spreadsheet usually requires substituting data values in the spreadsheet and then recalculating the spreadsheet, which can be burdensome and prone to mistakes. Also, such tables do not provide an easily perceived visual result that lends itself to intuitive analysis.

Therefore, there is a need for an integrated suite of tools that allow planners to assemble, manipulate and visualize large amounts of data used in the facilities planning process.

SUMMARY OF THE INVENTION

The disadvantages of the prior art are overcome by the present invention which, in one aspect, is a system for planning at a healthcare facility by a user. The system is operational on a digital computer that includes a computer readable memory. A database is stored on the computer readable memory. The database is configured to store health care facility impacting data including demographic data describing a preselected set of aspects of a population residing within a defined geographic area. A simulator, that is operable on the digital computer, is configured to apply a plurality of modeling tools to the health care facility impacting data and configured to generate output data corresponding to selected data in the health care facility impacting data and configured to store the output data in a predefined memory location. The plurality of modeling tools includes a protocols of care tool; a service configuration modeling tool; a financial analysis tool; and a facility modeling tool. A video monitor, responsive to the digital computer, is configured to display an image. The image includes a map that includes a visual representation of the geographic area and a plurality of dynamically configurable data display objects that are superimposed on the map. Each data display object is disposed adjacent to a location of a different one of a selected plurality of healthcare facilities and each display object is configured to display output data stored in the predefined memory location.

In another aspect, the invention is a healthcare facility planning system that includes a digital computer coupled to a computer readable memory and that is operable by a user. The system includes a database stored on the computer readable memory. The database is configured to store health care facility impacting data including demographic data describing a preselected set of aspects of a population residing within a defined geographic area. A simulator that is operable on the digital computer, is configured to apply a plurality of modeling tools to the health care facility impacting data and is configured to generate output data corresponding to selected data in the health care facility impacting data. The simulator is also configured to store the output data in a predefined memory location. The plurality of modeling tools includes a protocols of care tool configured to model an impact of changes in patient care protocols and configured to model facility space needs, operational costs savings, capital costs, staffing adjustment and projected patient volumes for the healthcare facility. The plurality of modeling tools also includes a service configuration modeling tool configured to analyze an impact on the selected healthcare facility by other healthcare facilities within the defined geographic area and configured to model patient volumes, market share, key rooms, and growth for the healthcare facility. The plurality of modeling tools also includes a financial analysis tool configured to analyze an impact on financial measures of the healthcare facility and configured to model charges, net revenue, direct fixed costs, direct variable costs, indirect fixed costs indirect variable costs, case mix, gross margin, net income, and average reimbursements for the healthcare facility. The plurality of modeling tools also includes a facility modeling tool configured to analyze an impact on facility need of the healthcare facility and configured to model current facility assessment, current key room inventory, infrastructure improvement costs, master facility program, projected facility needs, capital project program, projected capital project costs, projected impact on operational costs, and project return on investment for the healthcare facility. An output interface is responsive to the digital computer and is configured to display information generated by the simulator.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

DETAILED DESCRIPTION OF THE INVENTION

A preferred embodiment of the invention is now described in detail. Referring to the drawings, like numbers indicate like parts throughout the views. Unless otherwise specifically indicated in the disclosure that follows, the drawings are not necessarily drawn to scale. As used in the description herein and throughout the claims, the following terms take the meanings explicitly associated herein, unless the context clearly dictates otherwise: the meaning of "a," "an," and "the" includes plural reference, the meaning of "in" includes "in" and "on." Also, as used herein, "global computer network" includes the Internet.

Also, as used herein certain terms are defined as follows, unless their use clearly indicates otherwise:
Facility—A hospital, clinic or other healthcare related location used to provide services in one or more Service Lines.
Service Line—A grouping of services provided by a healthcare system such as Cardiology.
Service Type—Defines input and/or output units when analyzing Service Lines such as Beds,
Rooms or Admissions.
Bed Type—Defines bed categories associated with a Service Line and Facility.
Network—Used to define a set of facilities to be considered in one or more scenarios.
Scenario—A set of assumptions and facts to be applied to an analysis of facilities assigned to the scenario.

The system includes a facility planning tool that analyzes impacts of operations strategies and technology changes on inpatient volume, market shares, facility, operations and financial outcomes. As applied to the health services industry, one embodiment includes a system that integrates data used in health facilities planning. Such data can include data relating to local demographics, assumptions regarding future changes in demographics, capabilities of competing facilities and assumptions regarding possible changes in competitors' capabilities and the like. The system processes such information and presents relevant output on a graphic user display. The output data may be superimposed on a map to facilitate ease of understanding by users of the system.

Users are able to input changes to the input data and the system demonstrates the effect of such changes on the output from the system. Users are also able to make changes to the data used in generating the outputs without destroying the original underlying data. This allows the users to try different scenarios by changing the assumptions used in generating the output.

The system displays a scalable map of the area of interest. It may use a map generated by an existing on-line map service (for example, MICROSOFT VIRTUAL EARTH® or GOOGLE MAPS®). It displays elements of a user interface on top of the map. The user interface elements can be generated by existing interface software (for example, MICROSOFT ACCESS®).

Each of these user interface elements displays underlying data relating to facilities having a location on the map within a predetermined range of the user interface element. Also, each user interface element allows a user to input new data, which is then propagated throughout the system causing the other user interface elements to display new data resulting from the new data input by the user.

The user can input assumptions regarding such factors as growth and changing demographics. Using this information, the system can calculate the impact of different scenarios over an extended period of time.

Figure 1:
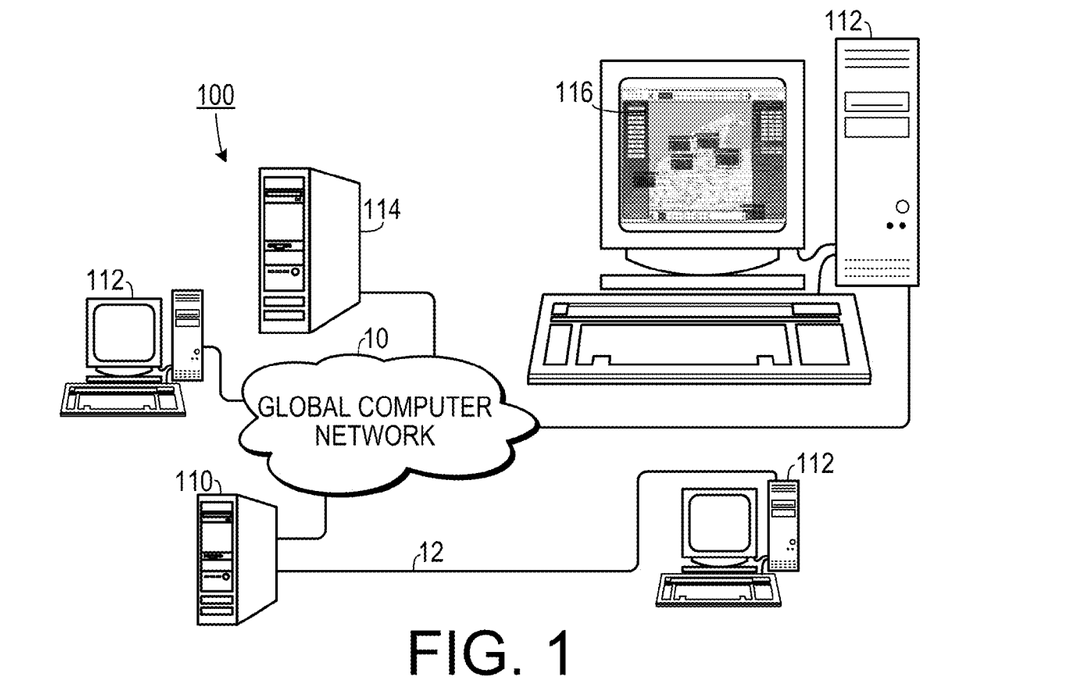
FIG. 1 is a schematic diagram of a configuration of a system for planning at a healthcare facility.

As shown in FIG. 1, in one embodiment of a healthcare facilities planning system 100, a central server 110 is coupled to a plurality of remote work stations 112 so as to be in data communication therewith. Each of the central server 110 and the remote work stations 112 include a computer-readable memory (such as random access memory, a hard drive, a flash drive, etc.) and a video monitor that is configured to provide an output interface display 116 to the user. A mouse and a keyboard may be employed as a user interface to allow the user to input data. The coupling may be through the global computer network 10, or through a hard-wired connection 12. The server 110 is configured to store a central database on a computer-readable storage medium, such as a hard drive. The server 110 is also configured to retrieve data (e.g., map data) from third party data servers 114 and integrate such data into the display 116 with data taken from the central database. In one example, third party data can include map data downloaded from an on-line map service.

The display also is part of a user interface includes data fields that allow individual users to input data values relating various scenarios. When a user inputs data regarding new assumptions, the server 110 recalculates the remaining data fields to demonstrate the impact of the new assumptions on the overall assessment. For example, a user can change a proposed number of beds in a cardiac care unit of a nearby hospital and the system will recalculate the impact of that increased bed count on a proposed new hospital. Similarly, users can change assumptions regarding such data points as projected population numbers, changing assumptions regarding aging patterns, the introduction (or closing) of a treatment unit at a nearby hospital, changing costs, etc. Such changes in the assumptions will result in changes in the impact associated with the assumptions and the impacts will be displayed in a manner that allows the user to see where and how the impact will be experienced. Based on this information, the users will be better able to make decisions regarding new facilities or changes to existing facilities.

The database stored on the computer readable memory is configured to store health care facility impacting data. This data can include demographic data describing the population residing within a defined geographic area, such as a metropolitan area, hospital data and marketing data. Such demographic information can include things such as: number of people currently in predefined age groups residing in the area; incidence of common medical conditions within the area; projected population growth in the area; etc. Other types of baseline data that is stored in the database can include things such as: usage rates experienced by other healthcare facilities in the area, which can be further broken down according to type of healthcare service used (e.g., general surgery, oncology, etc.); capacity of other healthcare facilities in the area, including according to type of healthcare services provided by each facility (e.g., cardiac care capacity, obstetrics capacity, etc.); current costs and projections for future costs.

Other types of baseline data that is stored in the database can include level of eligibility, level of adoption, patient throughput assumptions, space requirements, construction costs, operational costs and staffing ratios, demographic projections, patient acuity (patient acuity refers to the amount of time that a particular patient requires their doctors and nurses to spend with them in order to provide them appropriate care), average length of stay, protocols of care impact, space utilization, throughput, strategic growth rate, introduction of a new facility into a market, change of key room inventory, charges per patient, net revenue per patient, direct fixed per patient costs, direct variable per patient costs, indirect per patient fixed costs, indirect variable costs, case mix, assessment of current physical assets, projected inventory by key room, program elements, space benchmarks, construction costs, renovation costs, soft costs, costs escalation factors, project completion date, and amortization assumptions.

Figure 2:
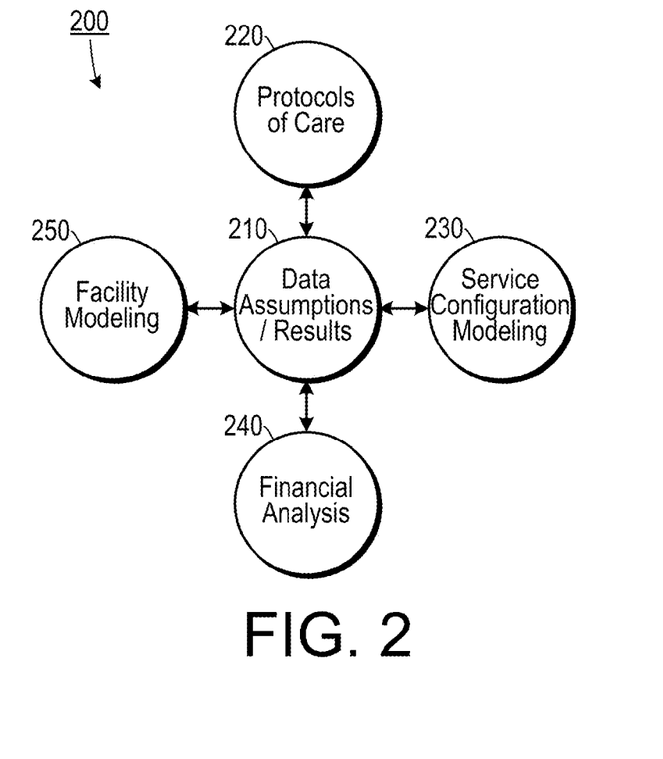
FIG. 2 is a block diagram of modeling tools employed in a simulator employed in one representative embodiment.

As shown in FIG. 2, the server 110 (or one of the workstations 112) is programmed to run a simulator 200 that applies modeling tools to the health care facility impacting data and configured to generate output data corresponding to selected data in the health care facility impacting data and configured to store the output data in a predefined memory location. The simulator is configured to run several tools that may be used by a healthcare facility to plan for use and expansion of facilities. One tool is a protocols of care tool 220 that models an impact of changes in patient care protocols and facility space needs, including operational costs savings, capital costs, staffing adjustment and projected patient volumes for the healthcare facility.

Another tool is a service configuration modeling tool 230 that analyzes the impacts on a healthcare facility by other healthcare facilities within the defined geographic area and models such things as: patient volumes, market share, key rooms, and growth for the healthcare facility. It analyzes patient, resource and facility data by service line and by facility. It also models the interrelationships among hospitals and services. It allows the user to study future capacity and to create various resources allocation scenarios.

A financial analysis tool 240 analyzes an impact on financial measures of the healthcare facility and models such things as: charges, net revenue, direct fixed costs, direct variable costs, indirect fixed costs indirect variable costs, case mix, gross margin, net income, and average reimbursements for the healthcare facility. A facility modeling tool 250 analyzes an impact on facility need of the healthcare facility and models such things as current facility assessment, current key room inventory, infrastructure improvement costs, master facility program, projected facility needs, capital project program, projected capital project costs, projected impact on operational costs, and project return on investment for the healthcare facility.

Figure 3:
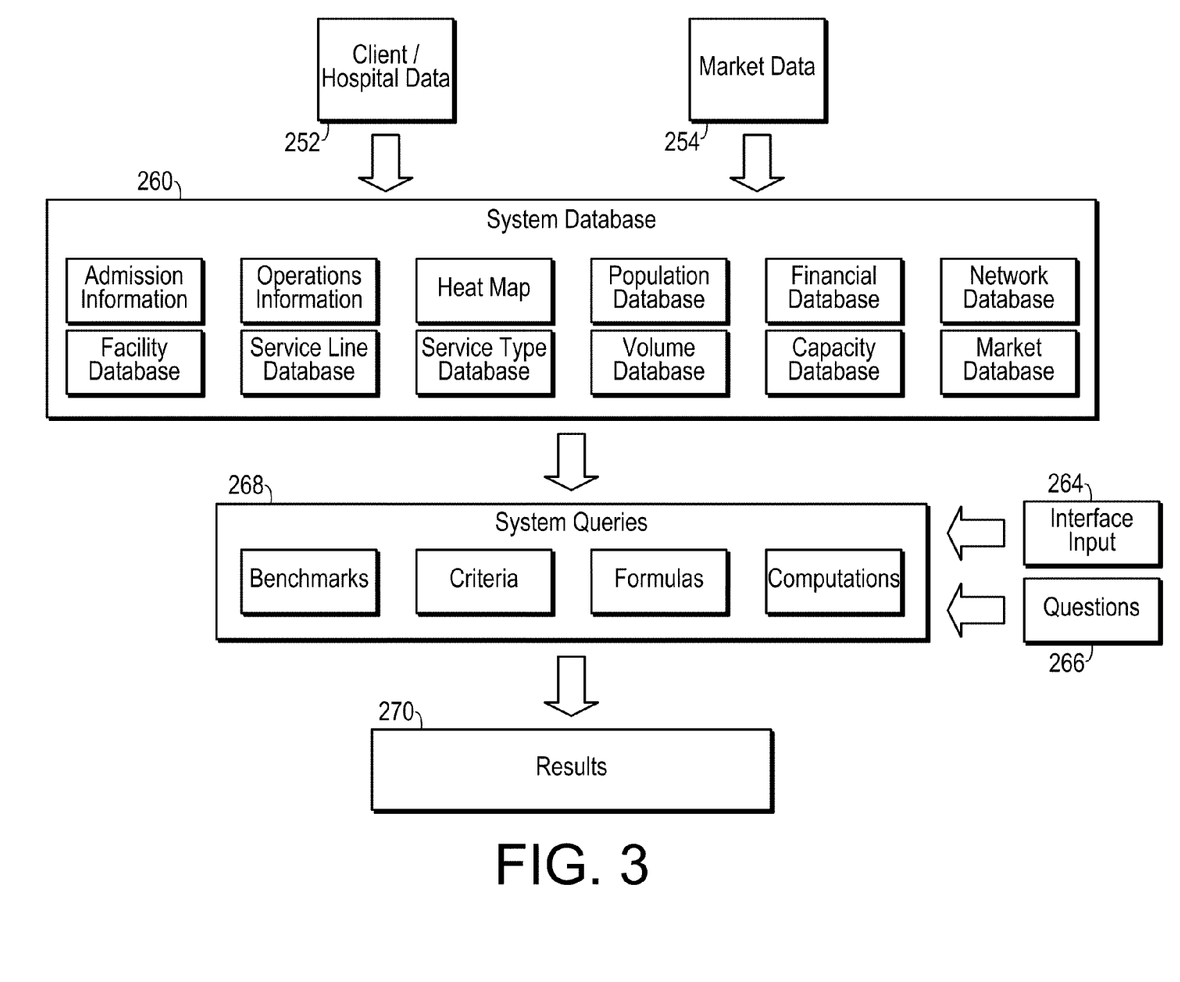
FIG. 3 is a diagram showing an overview of a data process employed in one embodiment.

As shown in FIG. 3, the system initially adds client and hospital data 252 and market data 254 into the system database 260. A commercially available database tool (e.g., MICROSOFT ACCESS®) may be used for the initial build of the database and for calculating the results from the stored data. Data can come from such sources as: raw data from a healthcare facility (e.g., discharge data), publicly-available demographic data (e.g., census data), and manually input data. Such data is can be sub-categorized, for example, in: admission information, operations information, a heat map, a population database, a financial database, a network database, a facility database, a service line database, a service type database, a volume database, a capacity data base and a market database. A user can input data through an input interface 264. The user can also generate structured questions 266 relating to data in the database 260. The system calculates responses to system queries 268 and generates output results 270 that can be displayed in data display objects and reports. When the user changes input data to generate an alternate scenario, the system saves the previous data, thereby allowing the user to revert to previous scenarios.

Figure 4:
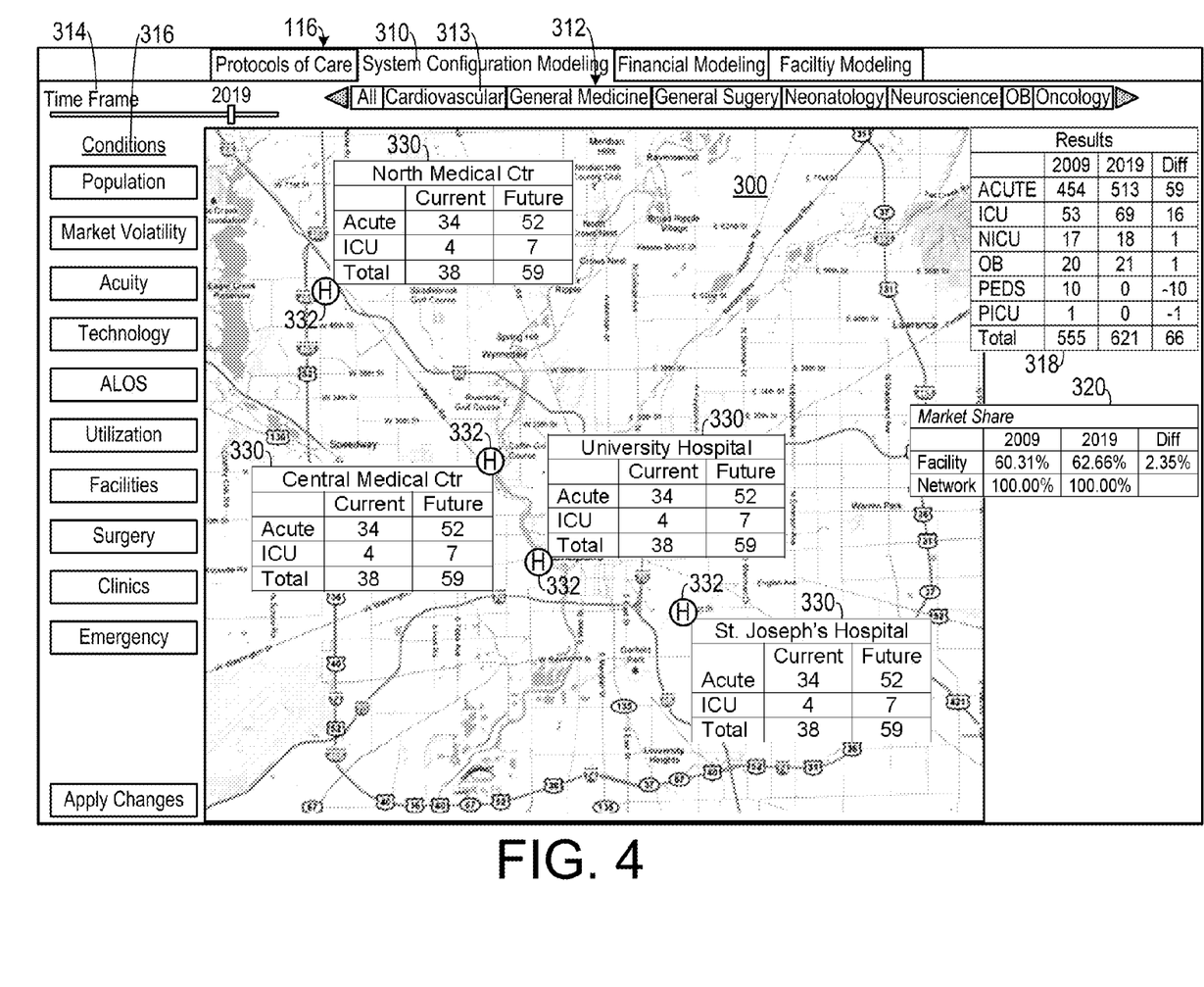
FIG. 4 is a diagram showing a user interface employed in one embodiment.

As shown in FIG. 4, on the display 116, the simulator is programmed to generate a dynamically configurable data display objects 330 that are superimposed on a digital representation of a map 300 of the predefined geographic area. The map 300 can be a digital map that is available from one of the many on-line map generating services. Each of the dynamically configurable data display objects 330 is displayed adjacent to the location of a corresponding healthcare facility on the map 300. A symbol 332 can provide a more precise indication of the location of the facility. Each display object 330 displays output data relating to the facility. The user can select exactly which data are to be displayed in the display objects 330 by clicking on conditions buttons 316 and selecting objects to be displayed. A timeframe sliding scale 314 allows the user to indicate how far into the future projections are to be made. The user can select which tool to invoke by clicking on a selected tool tab 310 and can even filter the simulation so as to consider only one or several of the medical services offered by a facility in question by clicking on a button 312 corresponding to the desired medical service. For example, if the user wants to consider only cardiovascular services, he would click on button 313. A results table 318 can show simulation results for a given healthcare facility. A market share assessment table 320 provides estimates the market share that could be experienced by the facility within a network.

The user can make changes to the data by entering new data into selected cells in one of the display objects 330 (such are regarding changed assumptions regarding a given facility) and the simulator will recalculate the data to determine the impact of such changed assumptions of all of the other selected facilities in the geographic area and display the results in the display objects 330. In addition to the display objects 330, the system can also produce user configurable reports and graphs showing predicted outcomes relating to the health care facility, based on the previously-collected data and assumptions entered into the database.

Figure 5:
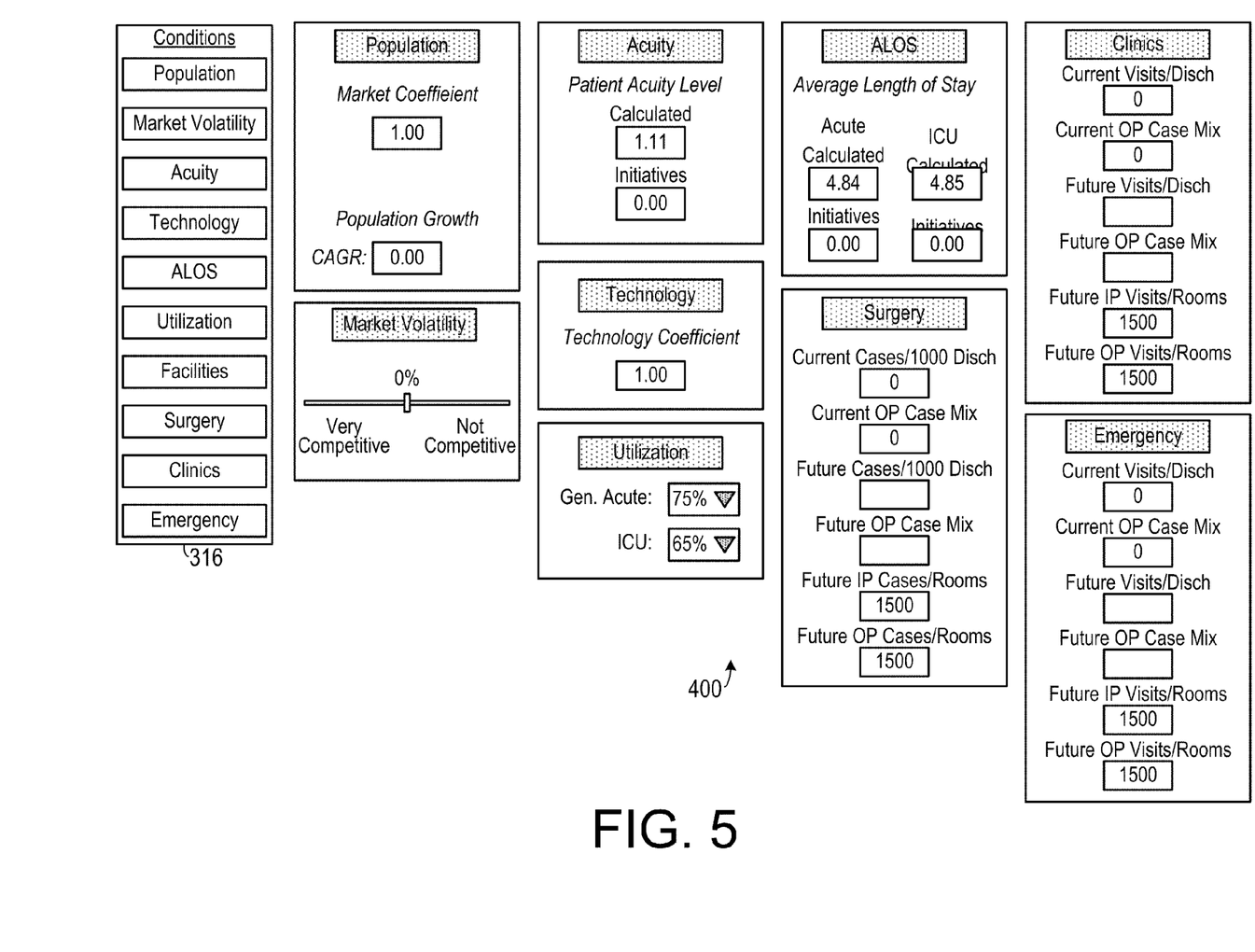
FIG. 5 is a diagram showing a data entry interface employed in one embodiment.

As shown in FIG. 5, several data entry windows 400 that open when the conditions buttons 316 are clicked. These data entry windows 400 allow a user to enter either currently known conditions regarding a health care facility or assumptions regarding the health care facility.

In one example, a user might desire to determine the impact of adding 20 patient beds to a cardiovascular unit at a given hospital over the next twenty years. The user would click on the cardiovascular service button 313 and enter the new number of beds (the current number plus 20) in the dynamic display object 330 corresponding to the facility of interest. The system would calculate the effect that this change would have on the other selected facilities and update their corresponding display objects 330. The user could also determine the effect that changing conditions would have on this scenario by clicking on a selected conditions button 316 and entering changed assumptions into the data fields in the data entry window corresponding to the selected button.

Figure 6:
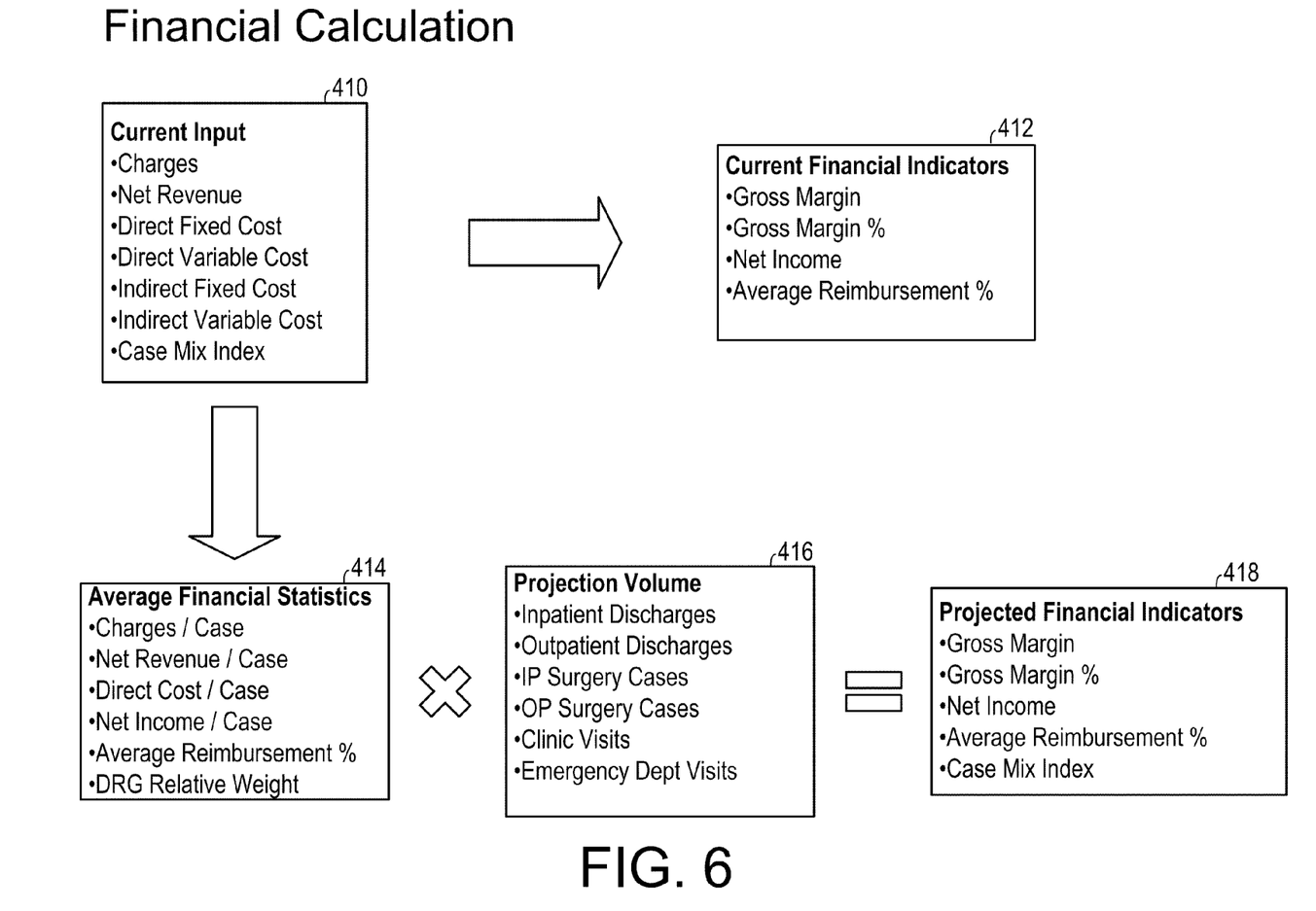
FIG. 6 is a diagram showing an approach to financial calculations employed in one embodiment.

As shown in FIG. 6, one example of how financial calculations are performed begins with the input of current data 410, which can include such items as: charges; net revenue; direct fixed cost; direct variable cost; indirect fixed cost; indirect variable cost; and case mix index. This can be used to derive current financial indicators 412, such as: gross margin; gross margin %; net income; and average reimbursement %. It can also generate average financial statistics 414, such as: charges per case; net revenue per case; direct cost per case; net income per case; average reimbursement %; and DRG relative weight. Selected items from the average financial statistics 414 can be multiplied by assumptions data relating to projected volume 416, which can include: inpatient discharges; outpatient discharges; IP surgery cases; OP surgery Cases; Clinic Visits; and Emergency Department Visits. The result is the projected financial indicators 418, which can include: gross margin; gross margin %; net income; average reimbursement %; and case mix index.

Some of the software components employed in the simulator include:
- A database defining relationships between the logical concepts/constructs;
- A data mining and analysis services tool providing an aggregation of data across time and applying business rules to provide estimates of future key performance indicator values;
- A rich internet application interface that includes internet enabled client interface providing a framework for user interaction with the analysis engine;
- Web Services that include server based tier providing a service based interface to the analysis engine; and
- Mapping and GIS interfaces that provide interactive mapping functionality used to indicate geographic location of facilities and to present facility related data.

The data tier describing the logical concepts and constructs are stored in a database along with data describing assumptions about growth in the market, distributions of services between facilities and the closing and opening of new facilities during the life of the scenario being considered. A snowflake schema may be used utilized to store the related fact and dimension tables. Additional information may be generated by applying business rules to the data stored in the database to produce a multi-dimensional analysis cube. The analysis cube contains measures of rooms, admissions and beds as well as other parametric measures for each year in the analysis. These data are provided across all facilities and service lines included in a scenario. Access to the data tier is provided by a web service based architecture.

The application interface (application tier) is a rich internet application that includes the following interface components:
- A control to allow user to select the scenario to be viewed;
- A scenario loading mechanism;
- A background map showing facility locations, facility types and selected analysis parameters for a specified year;
- A control to select the year for which data is to be viewed;
- A form based interface allowing the user to modify analysis assumptions such as growth and acuity factors;
- A form based interface allowing facility data to be created, updated and deleted;
- A reporting interface providing analysis results for a selected year in the analysis;
- A control providing the display of all service lines in the scenario allowing individual service lines to be selected for analysis;
- A control providing the display of all facilities in the scenario allowing individual facilities to be selected for analysis; and
- A series of financial reports and charts providing financial information across time, service lines and facilities. Reports and charts can be produced for selected facilities or sets of facilities.

The system consolidates healthcare facility information into a single database and creates an interface that calculates healthcare facility planning parameters in view of a plurality of alternate scenarios. The display objects allow the user to change assumptions by changing data in data fields selected by the user and then the simulator calculates the impact of the changed assumptions for all of the other facilities in the area, displaying the results in the other display objects. Because the system allows the user to manipulate several different variables at once, the user can see the results of several different scenarios quickly and without the confusion associated with viewing data on a spreadsheet. Thus, the user can see the effect that a changed assumption applied to one health care facility has on the surrounding health care facilities in an easy to understand format. The user can use the system to determine the impact of such things as expanding a healthcare facility, redeploying resources within a healthcare facility and building a new healthcare facility. The user could also determine such things a projected bed and facility needs and projected financial states that result from such activities. The outputs can also be projected over a long period of time in response to evolving assumptions regarding such things as demographics and technology.

In other embodiments, the system may be applied to other planning applications. For example, the system could be used to plan the new development or expansion of airports, business parks, colleges, etc.

The above described embodiments, while including the preferred embodiment and the best mode of the invention known to the inventor at the time of filing, are given as illustrative examples only. It will be readily appreciated that many deviations may be made from the specific embodiments disclosed in this specification without departing from the spirit and scope of the invention. Accordingly, the scope of the invention is to be determined by the claims below rather than being limited to the specifically described embodiments above.

What is claimed is:

1. A system for planning at a selected healthcare facility of a plurality of healthcare facilities by a user, operational on a digital computer including a computer readable memory, comprising:
    (a) a database stored on the computer readable memory, the database configured to store health care facility impacting data for a plurality of healthcare facilities within a defined geographic area, the impacting data including demographic data describing a preselected set of aspects of a population residing within the defined geographic area;

(b) a data entry interface configured to receive from the user new input healthcare facility impacting data corresponding to projected assumptions regarding changes in the health care facility impacting data regarding a selected healthcare facility of the plurality of healthcare facilities;

(c) a simulator, operable on the digital computer, that is configured to apply a plurality of modeling tools to the health care facility impacting data and the projected assumptions of the selected healthcare facility, the simulator further configured to generate output data indicative of an impact that the projected assumptions for the selected healthcare facility will have on non-selected healthcare facilities of the plurality of healthcare facilities in the defined geographic area and configured to store the output data in a predefined memory location, the plurality of modeling tools including:
(i) a protocols of care tool;
(ii) a service configuration modeling tool that is configured to model interrelationships among hospitals;
(iii) a financial analysis tool; and
(iv) a facility modeling tool; and (d) a video monitor, responsive to the digital computer, configured to display an image that includes:
(i) a map that includes a visual representation of the geographic area; and
(ii) a plurality of dynamically configurable data display objects, superimposed on the map, each of the plurality of display objects configured to display healthcare facility impacting data corresponding to a different one of the plurality of healthcare facilities and each display object disposed adjacent to a location of the healthcare facility to which it corresponds and each display object including a plurality of data fields that are configured to display output data from the simulator that is stored in the predefined memory location, the simulator configured, upon receipt of new input healthcare facility impacting data corresponding to projected assumptions about the selected healthcare facility received from the user, to calculate new output healthcare facility impacting data corresponding to each of the plurality of data display objects to determine an impact of the new healthcare facility impacting data received by the data entry interface on each of the dynamically configurable display objects, the simulator also configured to display results therefrom in each of the data fields included in each of the dynamically configurable display objects.

2. The system of claim 1, wherein the dynamically configurable data display objects further include a data input interface configured to receive a data input from the user and wherein the simulator is further configured to generate, based on the data input, revised data corresponding to the selected data in the health care facility impacting data and to store the revised data in a location so that the revised data is displayed in the dynamically configurable data display object.

3. The system of claim 1, wherein the image further includes in interactive condition select object configured to receive an input from the user that indicates conditions that the user desires to be imposed on the simulator.

4. The system of claim 3, wherein the simulator is further configured to project future performance of the healthcare facility based on a plurality of assumptions regarding future conditions.

5. The system of claim 1, wherein the protocols of care tool is configured to model an impact of changes in patient care protocols as a result of at least one variable of the health care facility impacting data selected from a list of variables consisting of: level of eligibility, level of adoption, patient throughput assumptions, space requirements, construction costs, operational costs and staffing ratios.

6. The system of claim 4, wherein the protocols of care tool is also configured to generate at least one output selected from a group of outputs consisting of: facility space needs, operational costs savings, capital costs, staffing adjustment and projected patient volumes.

7. The system of claim 1, wherein the service configuration modeling tool is configured to analyze an impact on the selected healthcare facility by other healthcare facilities within the defined geographic area as a result of at least one variable of the health care facility impacting data selected from a list of variables consisting of: demographic projections, patient acuity, average length of stay, protocols of care impact, space utilization, throughput, strategic growth rate, introduction of a new facility into a market, and change of room inventory.

8. The system of claim 7, wherein the service configuration tool is also configured to generate at least one output selected from a group of outputs consisting of: patient volumes, market share, and growth.

9. The system of claim 1, wherein the financial analysis tool is configured to analyze an impact on financial measures of the healthcare facility as a result of at least one variable of the health care facility impacting data selected from a list of variables consisting of: charges per patient, net revenue per patient, direct fixed per patient costs, direct variable per patient costs, indirect per patient fixed costs, and indirect variable costs.

10. The system of claim 9, wherein the financial analysis tool is also configured to generate at least one output selected from a group of outputs consisting of: charges, net revenue, direct fixed costs, direct variable costs, indirect fixed costs indirect variable costs, gross margin, net income, and average reimbursements.

11. The system of claim 1, wherein the facility modeling tool is configured to analyze an impact on facility need of the healthcare facility as a result of at least one variable of the health care facility impacting data selected from a list of variables consisting of: assessment of current physical assets, projected inventory by-room, program elements, space benchmarks, construction costs, renovation costs, soft costs, costs escalation factors, project completion date, and amortization assumptions.

12. The system of claim 11, wherein the facility modeling tool is also configured to generate at least one output selected from a group of outputs consisting of: current facility assessment, current room inventory, infrastructure improvement costs, master facility program, projected facility needs, capital project program, projected capital project costs, projected impact on operational costs, and project return on investment.

13. A healthcare facility planning system for planning at a selected healthcare facility of a plurality of healthcare facilities by a user, including a digital computer coupled to a computer readable memory, operable by a user, the system comprising:
(a) a database stored on the computer readable memory, the database configured to store health care facility impacting data for a plurality of healthcare facilities within a defined geographic area, the impacting data including demographic data describing a preselected set of aspects of a population residing within the defined geographic area;

(b) a data entry interface configured to receive from the user new input healthcare facility impacting data corresponding to projected assumptions regarding changes in the health care facility impacting data regarding a selected healthcare facility of the plurality of healthcare facilities;

(c) a simulator, operable on the digital computer, that is configured to apply a plurality of modeling tools to the health care facility impacting data and the projected assumptions of the selected healthcare facility, the simulator further configured to generate output data indicative of an impact that the projected assumptions for the selected healthcare facility will have on non-selected healthcare facilities of the plurality of healthcare facilities in the defined geographic area and configured to store the output data in a predefined memory location, the plurality of modeling tools including:

(i) a protocols of care tool configured to model an impact of changes in patient care protocols and configured to model facility space needs, operational costs savings, capital costs, staffing adjustment and projected patient volumes for the healthcare facility;

(ii) a service configuration modeling tool configured to analyze an impact on the selected healthcare facility by other healthcare facilities within the defined geographic area and configured to model patient volumes, market share, and growth for the healthcare facility;

(iii) a financial analysis tool configured to analyze an impact on financial measures of the healthcare facility and configured to model charges, net revenue, direct fixed costs, direct variable costs, indirect fixed costs indirect variable costs, gross margin, net income, and average reimbursements for the healthcare facility; and (iv) a facility modeling tool configured to analyze an impact on facility need of the healthcare facility and configured to model current facility assessment, current room inventory, infrastructure improvement costs, master facility program, projected facility needs, capital project program, projected capital project costs, projected impact on operational costs, and project return on investment for the healthcare facility; and (d) an output interface, responsive to the digital computer, configured to display information generated by the simulator, the output interface configured to display an image that includes:

(i) a map that includes a visual representation of the geographic area; and (ii) a plurality of dynamically configurable data display objects, superimposed on the map, each of the plurality of display objects configured to display healthcare facility impacting data corresponding to a different one of the plurality of healthcare facilities and each display object disposed adjacent to a location of the healthcare facility to which it corresponds and each display object including a plurality of data fields that are configured to display output data from the simulator that is stored in the predefined memory location, the simulator configured, upon receipt of new input healthcare facility impacting data corresponding to projected assumptions about the selected healthcare facility received from the user, to calculate new output healthcare facility impacting data corresponding to each of the plurality of data display objects to determine an impact of the new healthcare facility impacting data received by the data entry interface on each of the dynamically configurable display objects, the simulator also configured to display results therefrom in each of the data fields included in each of the dynamically configurable display objects.

14. The healthcare facility planning system of claim 13, where the health care facility impacting data further includes data describing: level of eligibility, level of adoption, patient throughput assumptions, space requirements, construction costs, operational costs and staffing ratios.

15. The healthcare facility planning system of claim 13, where the health care facility impacting data further includes data describing: demographic projections, patient acuity, average length of stay, protocols of care impact, space utilization, throughput, strategic growth rate, introduction of a new facility into a market, and change of room inventory.

16. The healthcare facility planning system of claim 13, where the health care facility impacting data further includes data describing: charges per patient, net revenue per patient, direct fixed per patient costs, direct variable per patient costs, indirect per patient fixed costs, and indirect variable costs.

17. The healthcare facility planning system of claim 13, where the health care facility impacting data further includes data describing: assessment of current physical assets, projected inventory by room, program elements, space benchmarks, construction costs, renovation costs, soft costs, costs escalation factors, project completion date, and amortization assumptions.

18. The healthcare facility planning system of claim 13, wherein the simulator is further configured to generate, for display on the output interface:

(g) a map that includes a visual representation of the geographic area; and (h) a plurality of dynamically configurable data display objects, superimposed on the map, each disposed adjacent to a location of a different one of a selected plurality of healthcare facilities and each display object configured to display output data stored in the predefined memory location.

19. The healthcare facility planning system of claim 13, wherein the dynamically configurable data display objects further include a data input interface configured to receive a data input from the user and wherein the simulator is further configured to generate, based on the data input, revised data corresponding to the selected data in the health care facility impacting data and to store the revised data in a location so that the revised data is displayed in the dynamically configurable data display object.

20. The healthcare facility planning system of claim 13, wherein the image further includes in interactive condition select object configured to receive an input from the user that indicates conditions that the user desires to be imposed on the simulator.

* * * * *